(12) United States Patent
Gordon et al.

(10) Patent No.: US 6,603,873 B1
(45) Date of Patent: Aug. 5, 2003

(54) DEFECT DETECTION USING GRAY LEVEL SIGNATURES

(75) Inventors: Naama Gordon, Ramat-Efal (IL); Gadi Greenberg, Tel Aviv (IL)

(73) Assignee: Applied Materials, Inc., Santa Clara, CA (US)

( * ) Notice: Subject to any disclaimer, the term of this patent is extended or adjusted under 35 U.S.C. 154(b) by 0 days.

(21) Appl. No.: 09/438,577

(22) Filed: Nov. 12, 1999

(51) Int. Cl.$^7$ .............................. G06K 9/03; G06T 7/60
(52) U.S. Cl. ........................................ 382/144; 382/149
(58) Field of Search .................................. 382/149, 144, 382/291, 204; 348/126, 87; 702/35; 250/559.07, 559.45, 559.46; 356/237.4, 237.5; 438/16

(56) References Cited

U.S. PATENT DOCUMENTS

| | | | | |
|---|---|---|---|---|
| 4,398,177 A | * | 8/1983 | Bernhardt | 382/193 |
| 4,870,357 A | * | 9/1989 | Young et al. | 324/770 |
| 4,907,282 A | * | 3/1990 | Daly et al. | 345/471 |
| 5,038,048 A | * | 8/1991 | Maeda et al. | 250/559.41 |
| 5,058,178 A | | 10/1991 | Ray | 382/8 |
| 5,137,362 A | | 8/1992 | LeBeau | 356/394 |
| 5,224,176 A | * | 6/1993 | Crain | 382/136 |
| 5,608,816 A | * | 3/1997 | Kawahara et al. | 348/126 |
| 5,872,870 A | | 2/1999 | Michael | 382/291 |
| 6,396,943 B2 | * | 5/2002 | Yamashita | 382/144 |
| 6,408,109 B1 | * | 6/2002 | Silver et al. | 382/190 |

FOREIGN PATENT DOCUMENTS

WO   WO 99/16010   4/1999   ............ G06K/9/00

\* cited by examiner

*Primary Examiner*—Brian Werner
*Assistant Examiner*—Ryan J. Miller
(74) *Attorney, Agent, or Firm*—McDermott, Will & Emery

(57) ABSTRACT

A method and apparatus for inspecting isolated features on a reticle is provided wherein the isolated features are analyzed for defects globally as individual, whole features, rather than locally, pixel-by-pixel. In one embodiment, the reticle is imaged to produce pixels having a gray level, and an isolated feature is identified. An energy value for the isolated feature to be inspected is calculated by summing the gray levels of its pixels. A plurality of scatter values for the feature in different directions in the feature is calculated based on the equilibrium center of the feature to produce a unique "signature" for the inspected feature. The energy and scatter values of the inspected feature's signature are then compared with energy and scatter values associated with a corresponding reference feature to determine whether a defect exists in the inspected feature.

59 Claims, 12 Drawing Sheets

|       |       |       |       |       |       |       |       |       |       |       |
|-------|-------|-------|-------|-------|-------|-------|-------|-------|-------|-------|
| (0,0) |       |       |       |       |       |       |       |       |       |       |
|       | (1,1) | (2,1) | (3,1) |       |       |       |       |       | (9,1) |       |
|       | (1,2) |       |       |       |       |       |       |       |       |       |
|       | (1,3) |       |       |       |       |       |       |       |       |       |
|       |       |       |       |       |       |       |       |       |       |       |
|       |       |       |       |       |       |       |       |       |       |       |
|       |       |       |       |       |       |       |       |       |       |       |
|       |       |       |       |       |       |       |       |       |       |       |
|       | (1,9) |       |       |       |       |       |       |       | (9,9) |       |
|       |       |       |       |       |       |       |       |       |       |       |

FIG. 9

| j=    | 1 | 2 | 3 | 4  | 5  | 6  | 7 | 8 | 9 |
|-------|---|---|---|----|----|----|---|---|---|
| i=1   | 0 | 0 | 0 | 0  | 0  | 0  | 0 | 0 | 0 |
| i=2   | 0 | 0 | 0 | 0  | 0  | 0  | 0 | 0 | 0 |
| i=3   | 0 | 0 | 0 | 0  | 0  | 0  | 0 | 0 | 0 |
| 4     | 0 | 0 | 0 | 16 | 47 | 14 | 0 | 0 | 0 |
| 5     | 0 | 0 | 0 | 40 | 55 | 20 | 0 | 0 | 0 |
| 6     | 0 | 0 | 0 | 12 | 22 | 10 | 0 | 0 | 0 |
| 7     | 0 | 0 | 0 | 0  | 0  | 0  | 0 | 0 | 0 |
| 8     | 0 | 0 | 0 | 0  | 0  | 0  | 0 | 0 | 0 |
| 9     | 0 | 0 | 0 | 0  | 0  | 0  | 0 | 0 | 0 |

FIG. 10

DEFECT DETECTION USING GRAY LEVEL SIGNATURES

FIELD OF THE INVENTION

The present invention relates to a method for inspecting photolithographic reticles used in the manufacture of semiconductor devices, and more particularly for inspecting isolated reticle features. The invention has particular applicability for in-line inspection of reticles with submicron design features.

BACKGROUND ART

Current demands for high density and performance associated with ultra large scale integration require submicron features, increased transistor and circuit speeds and improved reliability. Such demands require formation of device features with high precision and uniformity, which in turn necessitates careful process monitoring.

One important process requiring careful inspection is photolithography, wherein masks or "reticles", are used to transfer circuitry features to semiconductor wafers. Typically, a series of such reticles are employed in a preset sequence. Each photolithographic reticle includes an intricate set of geometric features or "features" corresponding to the circuit components to be integrated onto the wafer, such as chrome features on a glass substrate. Each reticle in the series is used to transfer its corresponding features onto a photosensitive layer (i.e., a photoresist layer) which has been previously coated on a layer, such as a polysilicon or metal layer, formed on the silicon wafer. The transfer of the reticle features onto the photoresist layer is conventionally performed by an optical exposure tool such as a scanner or a stepper, which directs light or other radiation through the reticle to expose the photoresist. The photoresist is thereafter developed to form a photoresist mask, and the underlying polysilicon or metal layer is selectively etched in accordance with the mask to form features such as lines or gates on the wafer.

Fabrication of the reticle follows a set of predetermined design rules set by processing and design limitations. These design rules define, e.g., the space tolerance between devices and interconnecting lines and the width of the lines themselves, to ensure that the devices or lines do not overlap or interact with one another in undesirable ways. The design rule limitation is referred to as the "critical dimension" (CD), defined as the smallest width of a line or the smallest space between two lines permitted in the fabrication of the device. The design rule for most ultra large scale integration applications is on the order of a fraction of a micron.

As design rules shrink and process windows (i.e., the margins for error in processing) become smaller, inspection and measurement of reticle features is becoming increasingly important, since even small deviations of feature sizes from design dimensions may adversely affect the performance of the finished semiconductor device. For example, features on the surface of the reticle include relatively large features such as lines that extend a substantial distance across the surface of the reticle for forming interconnection lines or gates, and small squares or "I" shapes (e.g., for forming contacts), whose largest dimension is only about 2 $\mu$m or less. Such small features, termed herein "isolated features", are particularly sensitive to dimensional variations.

FIGS. 1A–1D illustrate some typical defects of isolated features. FIG. 1A shows an undersized isolated feature, wherein the size of a non-defective feature is represented by a dotted line. FIG. 1B shows an isolated feature having an "extension" in one corner. FIGS. 1C and 1D show isolated features having a "bite" in a corner or a side, respectively.

Those skilled in the art recognize that a defect on the reticle, such as extra or missing chrome in small features as shown in FIGS. 1A–1D, may transfer onto the wafers during processing in a repeated manner, and therefore may significantly reduce the yield of the fabrication line. Therefore, it is of utmost importance to inspect the reticles and detect any defects thereupon. The inspection is generally performed by an optical system, such as the RT 8200 or ARIS-i reticle inspection system available from Applied Materials of Santa Clara, Calif. In the mask shop, i.e., where the masks and reticles are produced, the inspection system is used to scan the mask and compare the obtained image to the database used to create the mask. Differences between the image and the database are flagged as a suspect location.

More particularly, in typical prior art inspection schemes, the surface of the reticle is scanned with a charge-coupled device (CCD) and the resulting image is an array of data elements called "pixels", each pixel being assigned a "gray level" corresponding to its transmissivity when scanned by the CCD. In other words, each pixel is assigned a gray level proportional to the light transmitted by a portion of the reticle. For example, depending on the lighting technique used during scanning, a pixel located in the middle of a white feature will have a very high gray level, while a pixel in the space between features will have a low gray level, or vice versa. The pixels are typically analyzed one at a time and compared to pixels at the same respective location in a reference database to determine the existence of defects. The gray levels of each of the pixels of the inspected reticle are also compared to the gray levels of their neighboring pixels to detect the edges of features for dimensional measuring purposes.

Disadvantageously, conventional reticle inspection tools cannot always accurately or reliably detect defects in small isolated features. Prior art inspection tools lack the necessary sensitivity because they are limited to performing a "local" analysis of one pixel at a time. Furthermore, conventional reticle inspection tools typically require perfect "registration", or synchronization, between the pixel streams of the inspected data and the reference database to perform their analysis. Such registration is difficult and time-consuming, thereby slowing the inspection process and reducing production throughput.

There is a need for a simple, fast, cost-effective methodology for inspection of reticles that enables accurate detection of defects in isolated features.

SUMMARY OF THE INVENTION

An advantage of the present invention is the ability to reliably detect defects in isolated features or otherwise delimited areas without increasing inspection time.

According to the present invention, the foregoing and other advantages are achieved in part by a method of inspecting a target feature formed on a surface, the method comprising imaging the target feature to produce one or more target data elements representative of the target feature, each target data element having a gray level and associated with a respective location on the surface. An energy value for the target feature is calculated by summing the gray levels of the target data elements corresponding to the target feature, an equilibrium center of the target feature is determined, and then a plurality of scatter values, each in a different predetermined direction in the target feature, are calculated.

The target feature is thereafter identified as corresponding to a target reference feature, and the energy and scatter values of the target feature are compared with energy and scatter values in a historical database of previously inspected features associated with the target reference feature to determine whether a defect exists in the target feature.

Another aspect of the present invention is an inspection tool for carrying out the steps of the above method.

Additional advantages of the present invention will become readily apparent to those skilled in this art from the following detailed description, wherein only the preferred embodiment of the present invention is shown and described, simply by way of illustration of the best mode contemplated for carrying out the present invention. As will be realized, the present invention is capable of other and different embodiments, and its several details are capable of modifications in various obvious respects, all without departing from the present invention. Accordingly, the drawings and description are to be regarded as illustrative in nature, and not as restrictive.

BRIEF DESCRIPTION OF THE DRAWINGS

Reference is made to the attached drawings, wherein elements having the same reference numeral designations represent like elements throughout, and wherein:

FIG. 9 illustrates a pixel span for calculating projections from an origin in a method according to an embodiment of the present invention.

FIG. 10 illustrates the pixel gray levels and isolating frame for an isolated feature.

DESCRIPTION OF THE INVENTION

Figure 1A:
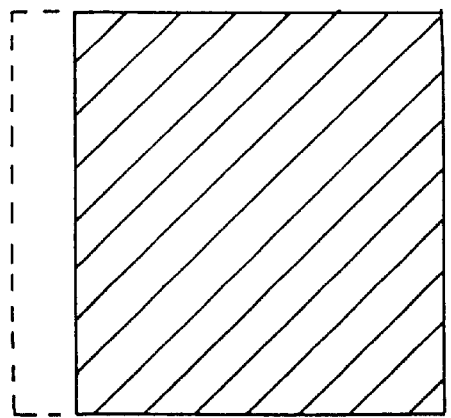
FIGS. 1A–1D illustrate possible defects of a feature on a reticle.

Conventional methodologies for inspecting features formed on the surface of a photolithographic reticle are not capable of accurately, reliably and economically detecting defects in isolated features, such as contacts having dimensions less than 2 $\mu$m. The present invention addresses and solves these problems by isolating a feature to be analyzed globally; i.e., as an individual whole feature, instead of locally, pixel-by-pixel, as in prior art inspection methodology. By analyzing features as whole features instead of as individual pixels, defect-sensitive inspection parameters that are properties of the entire isolated feature (e.g., energy and scatter about a particular axis) are calculated by the present methodology. The calculated inspection parameters are employed as a "signature" or characterizing vector of the inspected feature and compared, for example, with corresponding parameters of known non-defective comparable isolated features to reliably and accurately detect defects. Because the parameters employed are not dependent on registration between the inspected and reference feature pixel streams, complex and time-consuming registration procedures are not necessary when practicing the present invention, thereby decreasing inspection time and increasing production throughput.

According to the methodology of the present invention, a reticle is inspected using a conventional inspection tool, such as the RT 8200 or ARIS-i, which images a reticle (as with a scanning CCD array) as an array of pixels, each having a gray level. An isolated feature is detected by first performing edge detection in a conventional manner to determine the percentage of pixel area that is occupied by a feature, and then multiplying the percentage by the pixel's gray level to obtain the gray level value that is attributable to the feature for each pixel in the array (referred to herein as the "isolated format gray level"). Next, a selected pixel containing part of a feature, and all other pixels near it (e.g., within a 13×13 span of pixels), are analyzed to determine if they are part of an isolated feature by, for example, attempting to find a "frame" of background pixels (i.e., pixels representative of space on the reticle between features) surrounding the feature containing the selected pixel. If such a frame exists, then the pixels inside it represent an isolated feature.

After detecting an isolated feature and identifying its component pixels as described above, the value of selected "signature parameters" of the isolated feature are calculated. Such parameters can include dimensional characteristics of the isolated feature including width, height, diameter, etc., as well as mathematical characteristics and image-processing derived characteristics (e.g., frequencies). In one embodiment of the present invention, the weighted gray levels of the pixels belonging to the isolated feature are summed, yielding the energy parameter. The equilibrium center (i.e., center of mass) of the isolated feature with respect to an origin is then calculated, as well as the moments of inertia of the feature around axes in several directions in the pixel array that pass through the origin (e.g., the "x", "y", "slash" and "backslash" diagonal directions), and the moments of inertia of the feature around the axes in the several directions that pass through the equilibrium center. Finally, the "scatter" of the feature about the axes in the several directions that pass through the center of equilibrium are calculated.

The parameter values (i.e., energy and scatter values) of the inspected isolated feature are then compared to corresponding parameter values of previously inspected features of the same kind as the inspected feature, stored in a historical database, to detect defects in the inspected isolated feature. If any of the calculated parameters of the inspected feature differ from those in the historical database by more than a threshold amount for that parameter, the inspected isolated feature is deemed defective.

Thus, the gray level of each pixel of an image is converted to an isolated format gray level (by multiplying the gray level by the percentage of pixel area that is occupied by a feature), so the isolated format gray levels can be summed, such that all the relevant information of an isolated feature, and only the information of that isolated feature, is gathered. Since the inspection parameters of the isolated feature are calculated for the feature as a whole and not pixel-by-pixel (e.g., scatter values are calculated based on the center of equilibrium of the feature, and the energy does not depend on the location of the feature), registration with a reference database is not required for comparing the parameters to those in the historical database. Furthermore, for each parameter, a range of possible values can be determined for different types of isolated features. For example, a range of energy values can be determined for a 1 $\mu$m square contact, a 1.5 $\mu$m square contact, a 1 $\mu$m I-shaped feature, etc. Such information is used in the methodology of the present invention to compare parameters of an inspected isolated feature (e.g., a 1 $\mu$m contact, 1.5 $\mu$m contact, etc.) to typical parameters in the historical database.

Figure 1B:
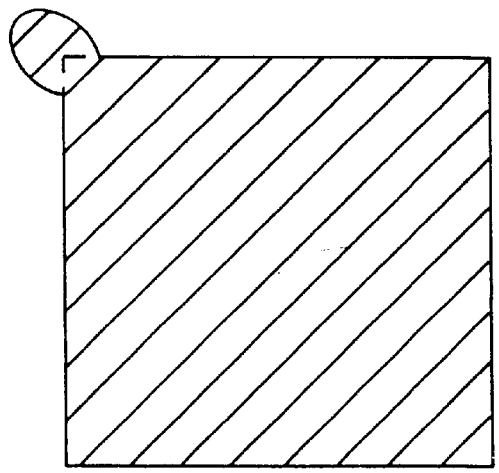
Figure 1C:
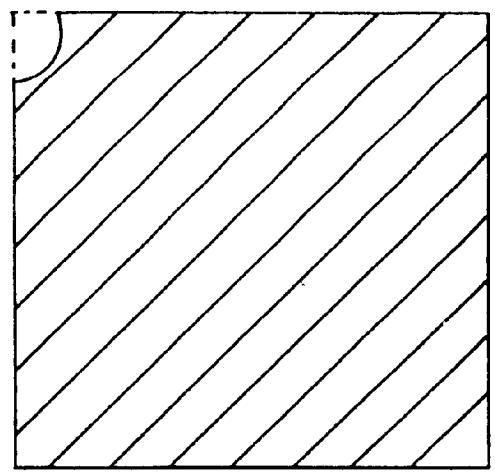
Figure 1D:
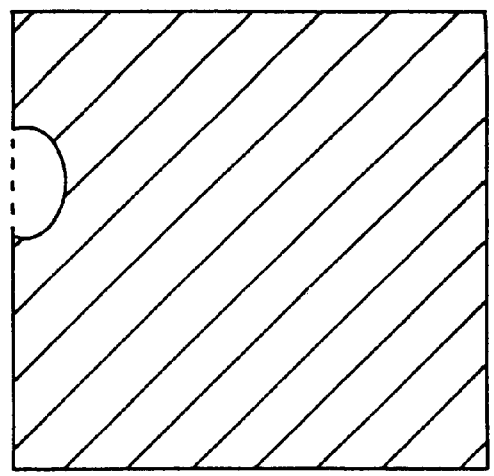

The energy parameter and scatter parameters, including scatter values calculated about axes in several directions (horizontally, vertically, or diagonally in a slash or backslash direction with respect to the array of pixels) are particularly useful for detecting defects in isolated reticle features because those parameters are sensitive to small variations in the size of the features, and are also sensitive to the presence of missing or extra portions of the features. The difference in significance of certain parameters depending on the nature of the defect is explained with reference to FIGS. 1A–1D. The undersized defect in FIG. 1A causes a change in the energy of the feature (depending on the amount of the feature that is missing) and a significant change in the scatter in the x-direction, but not much change in the scatter in the y-direction. On the other hand, the extended corner defect of FIG. 1B does not greatly affect the energy value, but has a large effect on scatter in the backslash direction. Likewise, the bite in the corner defect of FIG. 1C does not affect the energy to a great extent if the defect is small, but scatter in the backslash direction is decreased. The bite in the side of the feature shown in FIG. 1D, since it is not far from the center of the feature and affects many pixels, decreases the energy and the scatter in the x-direction.

Figure 2:
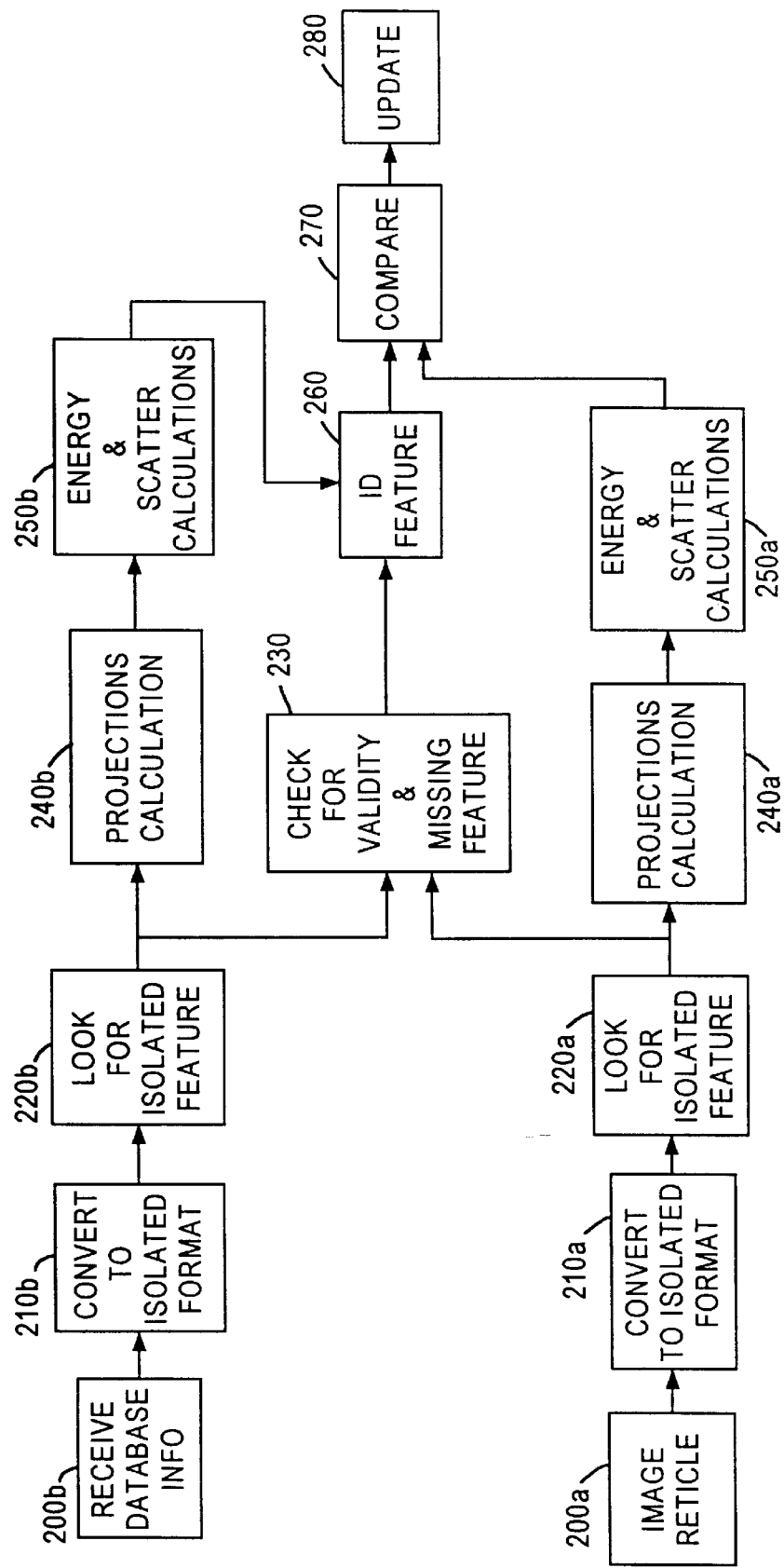
FIG. 2 is a flow chart illustrating sequential steps in a method according to an embodiment of the present invention.
Figure 3:
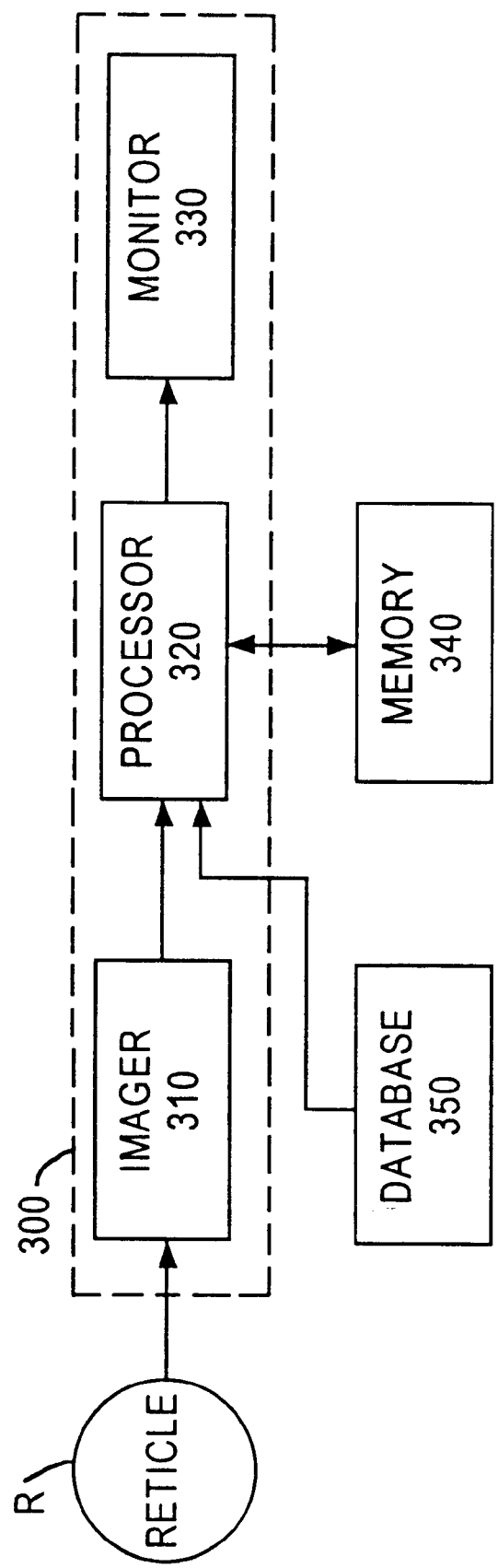
FIG. 3 is a block diagram that illustrates an embodiment of the invention.

An embodiment of the present invention utilizing the energy and scatter values of the isolated feature is illustrated in FIGS. 2–13. The present invention is implemented at an inspection tool 300, as shown in FIG. 3, comprising an imager 310 for imaging the surface of a reticle R at high speed, typically using a photo multiplier tube (PMT) or CCD and an illumination source such as a lamp or a laser. Reticle R, typically comprising metal features on a transparent substrate (such as chrome on a glass surface), can be imaged by transmitting light through the substrate to the CCD, by reflecting light from the features to the CCD, or both. Inspection tool 300 further comprises a processor 320, which preferably performs the analysis disclosed herein electronically, and a monitor 330 for displaying results of the analyses of processor 320. Processor 320 can be in communication with a conventional reticle reference design database 350 and a memory device 340, such as a semiconductor memory. The functions of processor 320 are preferably implemented in hardware such as logic gates, for increased speed compared to software-implemented processing.

FIG. 2 is a general overview of the defect detection process of the present invention. The inventive process has two major channels that are almost identical: a reference (database) channel at the top of the diagram, and an inspected channel at the bottom of the diagram. At step 200*a* in FIG. 2, reticle R is imaged by imager 310 in a conventional manner and the image received by processor 320, which processes the image as a plurality of data elements called "pixels", each pixel having a gray level and associated with a location on reticle R. Binary reference information corresponding to features on reticle R is received by processor 320 from database 350 at step 200*b* as pixels having gray levels.

Figure 4:
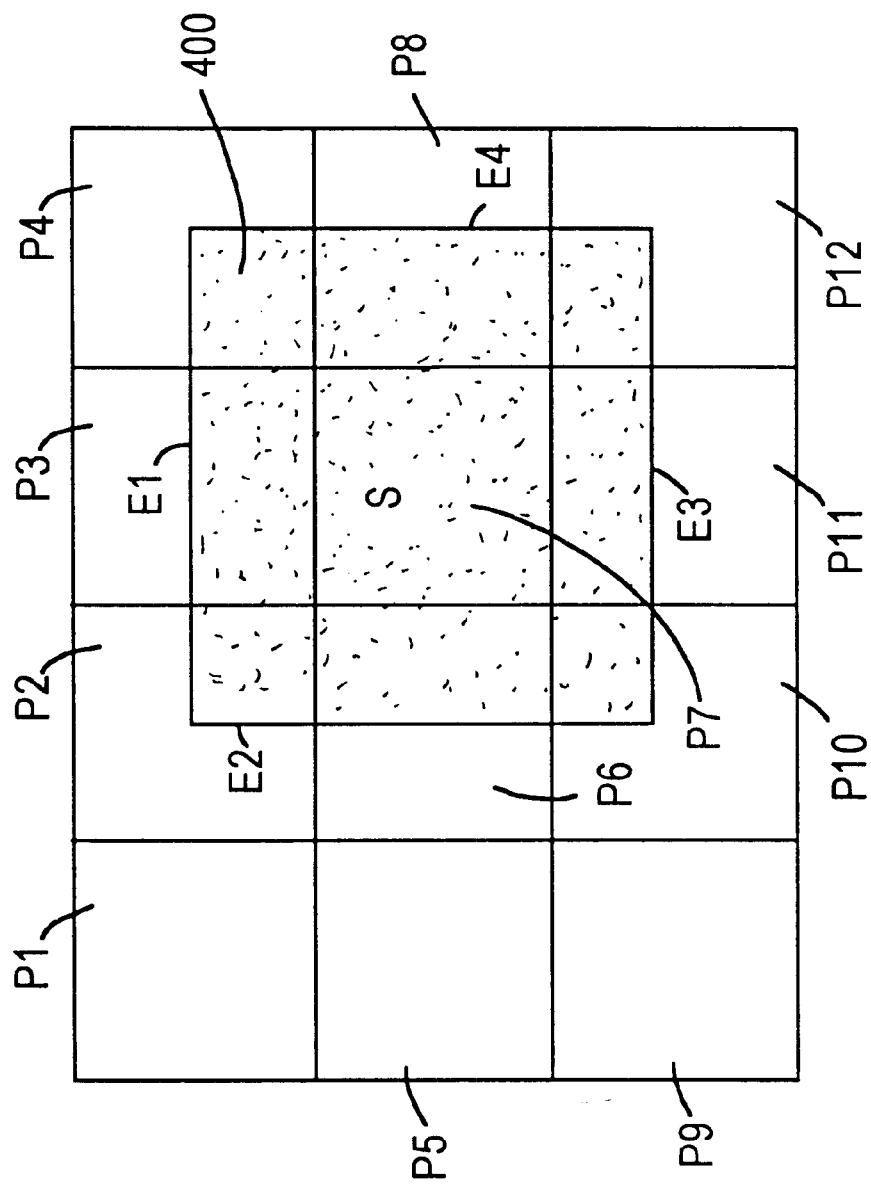
FIG. 4 illustrates the image-forming process used in practicing an embodiment of the present invention.

FIG. 4 represents an ideal isolated reticle feature 400 on reticle R (i.e., as feature 400 would appear in database 350), having edges E1–E4 and a surface S. The array of squares represents how pixels are formed, showing how much gray would be in each pixel P1–P12. An actual feature on reticle R corresponding to feature 400 would typically look similar to feature 400, with slight deviations such as corner rounding, proximity effects, etc. Pixels P1–P12 are typically a matrix of numbers representing the gray levels.

At step 210*a*, the pixels of the imaged features of reticle R are converted by processor 320 to an "isolated pixel format" by detecting the location of edges E1–E4 in each pixel P1–P12 in a conventional manner and multiplying the percentage of the area of each pixel P1–P12 containing a portion of feature 400 by the gray level of the pixel. At step 210*b*, binary data from database 350 is converted to the isolated pixel format. Edge detection does not need to be carried out at step 210*b*, since the location of edges is contained in database 350.

At steps 220*a*, 220*b*, the pixels of both channels are examined by processor 320 for the presence of an isolated feature, and at step 230 it is determined if a "missing feature" defect is present, and if a valid isolated feature has been found at steps 220*a*, 220*b*. If an isolated feature has been found, processor 320 calculates the projection of each pixel in the isolated feature from an origin in steps 240*a*, 240*b*, then calculates energy, center of gravity and several scatter parameters at steps 250*a*, 250*b*.

The calculated energy and scatter parameters from the reference channel are then used by processor 320 to identify the isolated feature at step 260. A "history" database of energy and scatter parameters of previously inspected features associated with the identified feature is then compared with the energy and scatter values of the inspected feature at step 270 to determine if a defect in the inspected feature exists. If the inspected feature is not defective, its energy and scatter values are added to the historical database at step 280.

Figure 5:
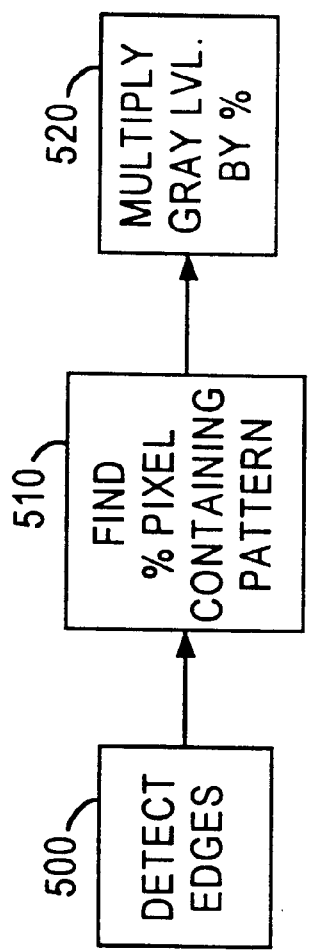
FIG. 5 is a flow chart illustrating sequential steps for converting pixels to an isolated format in a method according to an embodiment of the present invention.

Step 210*a*, wherein pixels from a reticle to be inspected are converted to an isolated pixel format by combining feature edge detection and pixel gray level, will now be described in greater detail with reference to FIG. 4 and the flow chart of FIG. 5. At this step, the gray level attributable to a pixel of the feature is determined for each pixel, thereby allowing isolated features to be identified and analyzed for defects.

At step 500, a selected pixel, e.g., pixel P2 in FIG. 4, is analyzed using a conventional edge-detection method, such as the "canny" method, to determine where the feature edges E1, E2 lie within pixel P2. Next, at step 510, it is determined, using the edge location information from step 500, the percentage of pixel P2 that contains a feature, depending on the "polarity" of the pixel. Since, as discussed above, reticles typically comprise chrome features, such as feature 400, on a glass surface, when imaged as with transmitted light, the glass which transmits lights is seen as white and the chrome which blocks the light (i.e., feature 400) is seen as black. Therefore, measurements are conventionally taken, as by processor 320, on both black and white features, and each measurement is assigned a polarity depending on whether it is white or black. At step 520, the gray level of pixel P2 is multiplied by the percentage from step 510 to obtain the isolated format gray level of pixel P2.

Figure 6:
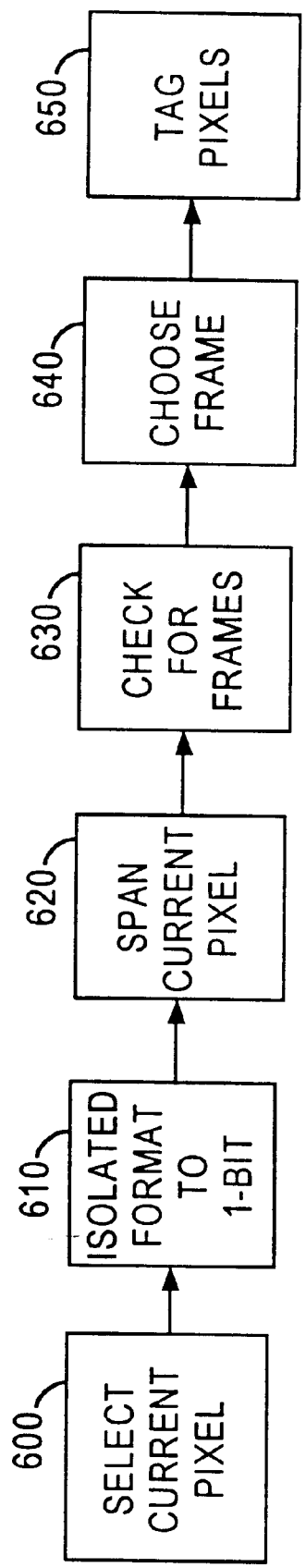
FIG. 6 is a flow chart illustrating sequential steps for detecting an isolated feature in a method according to an embodiment of the present invention.

Next, the isolated feature detection process of steps 220*a*, 220*b* or FIG. 2 will be described in greater detail with reference to FIGS. 6 and 7. When the surface of reticle R is imaged by CCD, or data representative of the surface of a defectless reticle is received by processor 320 from database 350, the result is an array of pixels representative of features on the surface and of the spaces separating the features. At steps 220*a*, 220*b*, the pixels, in isolated pixel format from steps 210*a*, 210*b*, are sequentially examined to determine whether they belong to an isolated feature.

At step 600, a pixel is selected, and at step 610 it is assigned a binary value (e.g., 0 or 1) based on its gray level to identify it as a pixel that is part of a feature or a pixel that is part of a space in between features. For example, the selected pixel is compared to a predetermined threshold gray level, and the pixel is determined to be a "black" or "white" pixel (i.e., a pixel corresponding to a space between features) if its gray level is less than the threshold gray level.

Next, at step 620, a span of pixels surrounding the current pixel is chosen for analysis. The span is a square array of pixels such as an 11×11 or 13×13 array, with the current pixel in the middle. The larger the span, the larger the isolated features which can be analyzed by the present invention. However, if it is preferred to realize the present invention in hardware (e.g., if processor 320 is preferred to be implemented as a plurality of logic gates), a larger span will result in more complex circuitry.

Figure 7A:
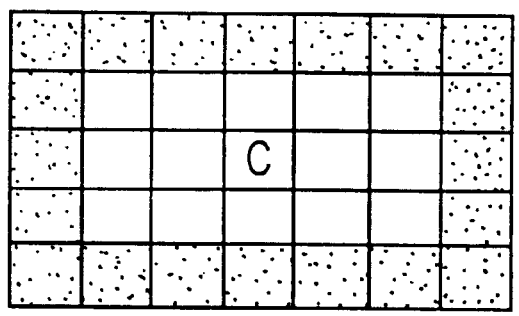
FIGS. 7A–7D illustrate pixel spans used for detecting an isolated feature in a method according to an embodiment of the present invention.
Figure 7B:
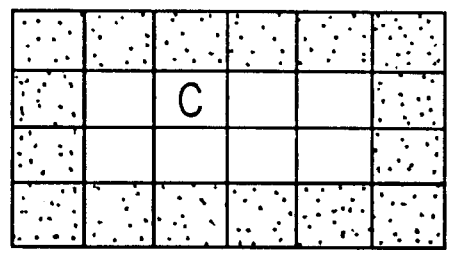
Figure 7C:
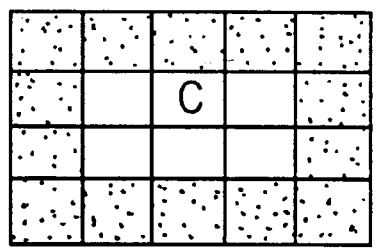
Figure 7D:
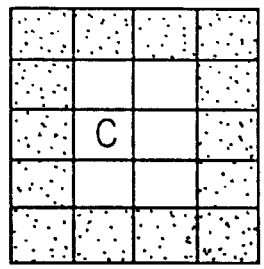

It is assumed, for purposes of this explanation, that substantially white features exist on a substantially black background. However, the present invention can be practiced using a different color polarity. At step 630, the pixels of the chosen span are analyzed to identify a "frame" of contiguous black (i.e., dark) pixels surrounding a window of one or more gray or white pixels corresponding to an isolated feature. For example, all possible frames around the current pixel are examined to find a black frame, if one exists, in which the current pixel is exactly in the middle when the height or width dimension is odd and up or to the left from the window center point when the height or width dimension is even. Such frames are illustrated in FIGS. 7*a*–7*d*, wherein the current pixel is denoted by "C". FIG. 7*a* shows a frame where the height and width are odd (5×7). FIG. 7*b* shows a frame where the height and width are even (4×6). FIG. 7*c* shows a frame where the height is even and the width is odd (4×5). FIG. 7*d* shows a frame where the height is odd and the width is even (5×4). FIGS. 7*a*–7*d* show the frame as a black frame surrounding white pixels; however, the frame can be white and the pixels inside it black, depending on the feature.

After all the possible frames are checked at step 630 (e.g. 100 possible frames for an 11×11 span), if contiguous frames are found, the smallest frame is chosen as the "blocking frame" (see step 640) and the pixels inside it are "tagged" as belonging to an isolated feature for further processing, as by an "isolated feature indicator bit" (step 650). Pixels that are not part of an isolated feature are also tagged as such by the isolated feature indicator bit.

Referring again to FIG. 2, after performing steps 220*a* and 220*b* (i.e., after performing feature isolation on the reference and inspected channels), isolation-indication data processing is carried out at step 230. This step will now be described in detail with reference to FIG. 8. The purpose of this step is to synchronize the reference channel and the inspected channel while checking for a missing feature defect, as well as to ensure that a given feature is processed only once, and not multiple times. Mis-registration can occur between the pixel streams of the database and the inspected image (e.g., an offset of one or two pixels). If such mis-registration occurs, the pixels of the inspected reticle image are not at their expected location vis-à-vis the database pixels. At step 230, processor 320 searches for an isolated inspected feature if an isolated feature is found in the reference database, utilizing the isolated feature indicators in the reference and inspected channels. If an isolated inspected feature is not found in the proximity of where it should be according to the reference database, a missing feature defect is indicated.

As discussed above, in conventional reticle inspection methodologies, two streams of pixel data, one from the sample under inspection and the other from a reference database, must be perfectly synchronized (i.e., "registered") to properly carry out defect detection. Typically, this requires a complex and time-consuming process comprising performing a global registration at the pixel level, then performing sub-pixel registration by estimating what the gray level of the inspected pixel would be if the two data streams were perfectly aligned. In contrast, the present methodology requires only a general alignment between the reference and inspected channels, and can tolerate relatively large errors, depending on the proximity of features to each other. For example, the alignment can be one or two pixels "off" as long as the features on the reticle under inspection are not less than four pixels apart. This tolerance for error in registration is a major advantage of the present invention, since it greatly simplifies the inspection process while significantly decreasing inspection time.

Figure 8:
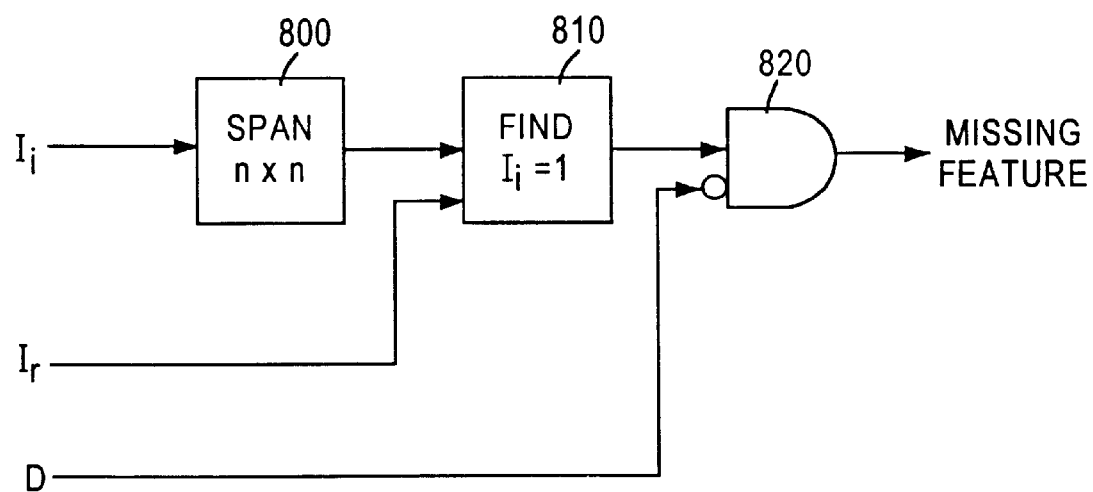
FIG. 8 is a flow chart illustrating sequential steps for matching an isolated feature to a reference feature in a method according to an embodiment of the present invention.
Figure 11:
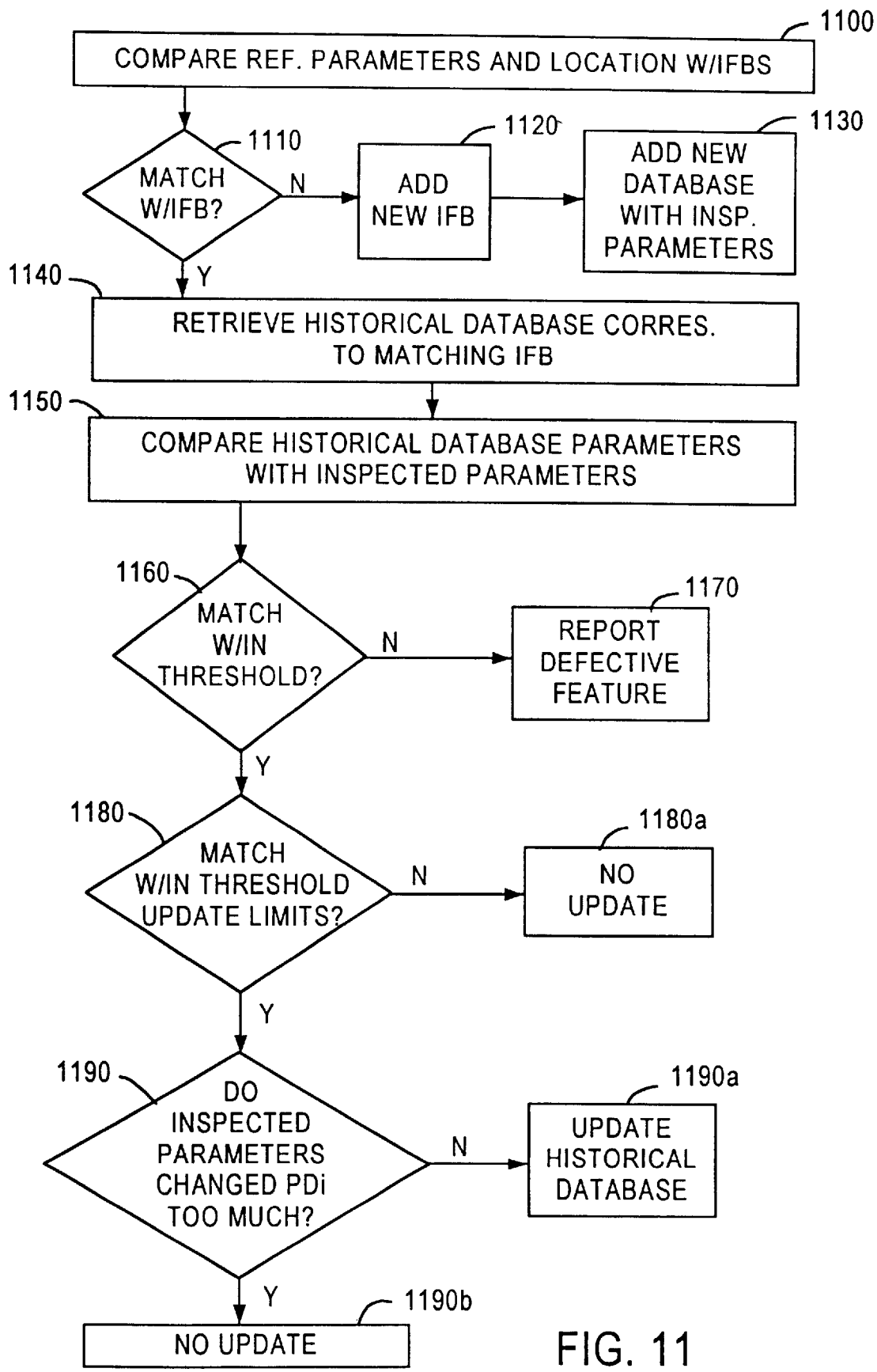
FIG. 11 is a flow chart illustrating sequential steps for detecting defects in a method according to an embodiment of the present invention.

Referring now to FIG. 8, at step 800 the inspected channel isolated feature indicator Ii for the current pixel is spanned to n×n pixels (e.g., n=1, 3 or 5) around the current pixel, and the isolated feature indicators of the pixels of the span are checked at step 810. If the reference channel isolated feature indicator Ir is "1", indicating that an isolated feature should be at that location in the inspected reticle, and there is no "1" in the n×n span, a missing feature defect is identified, unless a disable signal D is sent from the reference database (see step 820). Disable signal D is sent when the feature in the database is too large to be isolated; that is, if it is larger than a predetermined size, typically slightly smaller than the span of step 620 described above.

Referring again to FIG. 2, if an isolated feature is found in the proper place on the inspected reticle R, the projections of the gray levels (e.g., in the x, y, slash and backslash directions) are calculated at steps 240*a*, 240*b* for the isolated feature in the database and inspected channels. The projections are the sum of the gray levels of the pixels in a column, row or diagonal of the matrix of pixels which contains an isolated feature. FIG. 9 is an example of an 11×11 array of pixels representing an isolated feature, wherein the number pairs in brackets are the row and column numbers. Hereinafter, "j" refers to a column number, "i" refers to a row number, and "k" refers to a diagonal number. The projections are calculated as follows:

Pxj is the sum of the gray levels of the j-th column in the span (j=1 to 11)

Pyi is the sum of the gray levels of the i-th row in the span (i=1 to 11)

Pbsk is the sum of the k-th backslash-direction diagonal starting from the upper-left pixel (1,1) (k=1 to 21)

Next, at steps 250*a*, 250*b*, energy, center of equilibrium and scatter calculations are performed using the projections. Using the 11×11 span of FIG. 9 as an example, the energy E is calculated by:

$$E = \sum_{i=1}^{n=11} Pxi$$

The equilibrium center with respect to origin (0,0) is calculated by:

$$xe = \frac{\sum_i (i \cdot Pxi)}{E} \qquad ye = \frac{\sum_j (j \cdot Pyj)}{E}$$

The moments of inertia about axes in the Ix, Iy, Ibs in the x, y and backslash directions, respectively, which pass through the origin (0,0) are calculated by:

$$Ix = \sum_i i^2 Pxi \quad Iy = \sum_j j^2 Pyj \quad Ibs = \frac{1}{2}\sum_{k=2}^{2n=22} k^2 \cdot Pbsk$$

The moments of inertia Ixcm, Iycm, Ibscm about axes in the x, y and backslash directions that pass through the equilibrium center (xe,ye) are calculated by:

$$Ixcm = Ix - xe^2 \cdot E$$
$$Iycm = Iy - ye^2 \cdot E$$
$$Ibscm = Ibs - \frac{(xe+ye)^2}{2} \cdot E$$

The scatters Sx, Sy, Sbs, Ssl about the axes in the x, y, backslash and slash directions that pass through the equilibrium center (xe, ye), respectively, are calculated by:

$$Sx = \frac{Ixcm}{E} \quad Sy = \frac{Iycm}{E} \quad Sbs = \frac{Ibscm}{E} \quad Ssl = Sx + Sy - Sbs$$

For ease of implementing the present invention in hardware, it is preferred to combine the foregoing formulas, thereby enabling the energy and scatter values (which are the relevant parameters used for defect detection in this embodiment of the present invention) to be calculated directly with only two formulas. Thus, after the energy E is calculated, the scatter values are calculated as follows:

$$Sx = \frac{\sum_{j=1}^{11} j^2 \cdot Pxj}{E} - \left(\frac{\sum_{j=1}^{11} j \cdot Pxj}{E}\right)^2$$

$$Sy = \frac{\sum_{i=1}^{11} i^2 \cdot Pyi}{E} - \left(\frac{\sum_{i=1}^{11} i \cdot Pyi}{E}\right)^2$$

$$Sbs = \frac{\sum_{k=1}^{21}(k+1)^2 \cdot Pbsk}{2E} - 0.5 \cdot \left(\frac{\sum_{j=1}^{11} j \cdot Pxj + \sum_{i=1}^{11} i \cdot Pyi}{E}\right)^2$$

The following is a numerical example of such a calculation, with reference to FIG. 10, wherein the numbers in the cells represent the gray levels of their respective pixels. First, the projections are calculated:

9 Pxj's are: 0, 0, 0, (16+40+12=68), (47+55+22=124), (14+20+10=44), 0, 0, 0,

9 Pyi's are: 0, 0, 0, (16+47+14=77), (40+55+20=115), (12+22+10=44), 0, 0, 0

17 Pbsk's are: 0, 0, 0, 0, 0, 0, 16, (40+47=87), (12+55+14=81), (22+20=42), 10, 0, 0, 0, 0, 0, 0

The energy E is then calculated:

$E = 68+124+44=236$

The scatter values are calculated:

$Sx = (4^2 x68 + 5^2 x124 + 6^2 x44)/236 - ((4x68 + 5x124 + 6x44)/236)^2 = 0.4642$

Sy is a similar calculation.

$Sbs = (8^2 x6 + 9^2 x87 + 10^2 x81 + 11^2 x42 + 12^2 x10)/(2x236) - 0.5((4x68 + 5x124 + 6x44 + 4x77 + 5x115 + 6x44)/236)^2 = 0.4645$

Figure 12:
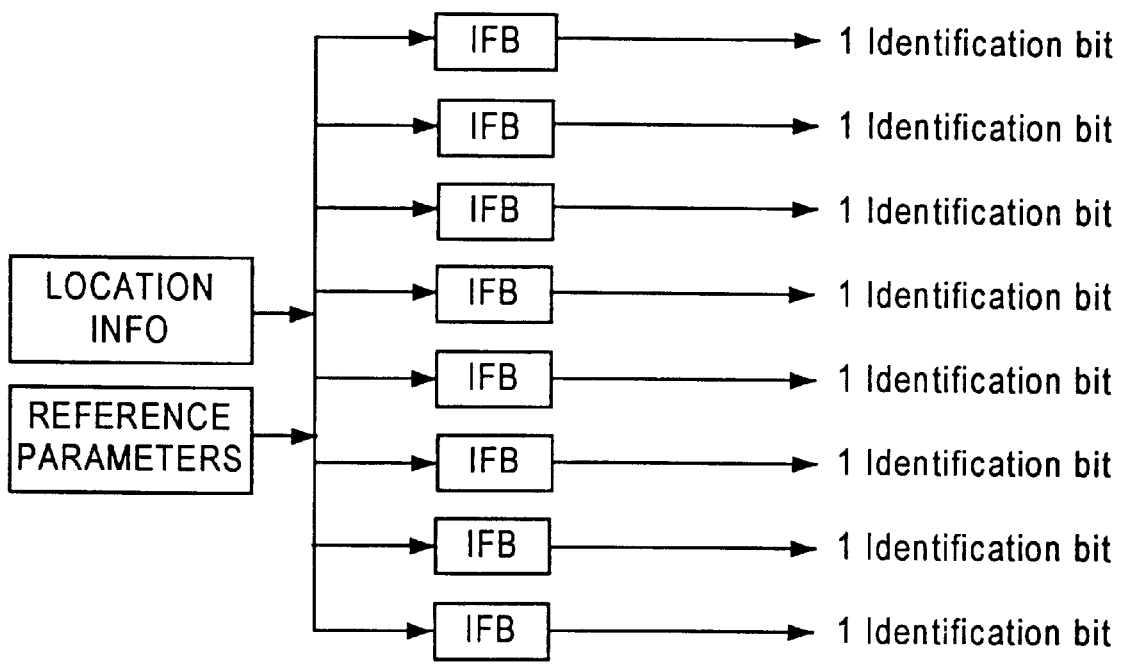
FIG. 12 illustrates identification feature blocks according to an embodiment of the present invention.

As illustrated in FIG. 2, after the energy and scatter parameters for both the isolated reference and inspected features have been calculated at steps 250*a*, 250*b*, the five reference feature parameters (i.e., energy and four scatter parameters) together with the reference feature's location on the CCD (i.e., the location of the diode which detected the feature) are used to identify the feature at step 260. This step will be described in greater detail with reference to FIGS. 11 and 12. At step 1100, the five reference parameters and the location information of the reference feature are compared with reference parameter sets called "identification feature blocks" (IFB) as shown in FIG. 12. Each IFB corresponds to a different isolated feature expected to be found on reticle R; for example, a 1 μm contact, a 2 μm contact, a 1 μm I-shaped feature, a 2 μm I-shaped feature, etc. In FIG. 12 there are, for example, eight features that can be positively identified. Each IFB is associated with a separate historical database of energy and scatter parameters of previously inspected features of its kind (e.g., stored in memory 360). If the isolated reference feature is identified at this step, the inspected feature's parameters will be compared to the appropriate historical database to determine if the inspected feature is defective.

Each of the five reference parameters are compared at step 1100 with a corresponding parameter in each of the IFBs separately, and the difference is compared to a predetermined threshold value. Additionally, the reference feature's location on the CCD is compared to a predetermined range of locations on the CCD where that IFB's feature can appear. For each IFB, if any of the five parameter comparisons yields a difference above the threshold value or the location examination shows that the reference feature's location is outside the location range, that IFB does not identify the feature. On the other hand, if the parameters and the locations match within the predetermined limits, the feature is identified, and the identification bit for that IFB is set.

In one embodiment of the present invention, if none of the IFBs match the reference feature at step 1110, a new IFB is added at step 1120 using the isolated reference feature's energy and scatter values as the new IFB's reference parameter set. At step 1130, a new historical database is added using the energy and scatter values of the isolated inspected feature. Thus, in a new reticle design, historical data for a new feature not previously in the database can be added to a new IFB.

If the isolated reference feature is identified (i.e., if its parameters match those of one of the IFBs), then at step 1140 the historical database associated with the matching IFB is retrieved by processor 320, and the energy and scatter values of the isolated inspected feature are compared with those of the historical database (see step 1150). Step 1150 corresponds to step 270 of FIG. 2. At step 1160, it is determined whether the parameters of the isolated inspected feature match the respective parameters of the historical database within a predetermined defect threshold for each feature. If any of the five inspected parameters falls outside its defect threshold, the feature is deemed defective at step 1170.

If the five inspected energy and scatter values are within the non-defect thresholds, at step 1180 it is then determined whether each of them fall within a predetermined "updating threshold", which represents the maximum amount of difference tolerated between the inspected parameter value and the historical database parameter value for updating purposes. If the difference between each of the inspected feature parameters and the respective parameter from the historical database is smaller than the updating threshold, at step 1190 the inspected feature parameters are eligible to be used to update the historical database, according to a weighted formula (see steps 1190a, 1190b). However, if the difference is larger than the updating threshold, the inspected parameters are not used to update the historical database (see step 1180a), since they will unacceptably skew the historical database.

The above-described embodiment of the present invention determines if a defect exists in the isolated feature based on the isolated feature's energy and scatter values. However, it should be realized that other calculated parameter values of the isolated feature can be used instead of, or in addition to, the energy and scatter values. For example, dimensions of the isolated feature such as its diameter, perimeter, radius, height, and/or width can be used, depending on the sensitivity of the calculated parameters to relevent variations in the characteristics of the feature, as determined by the user of the present invention.

Figure 13:
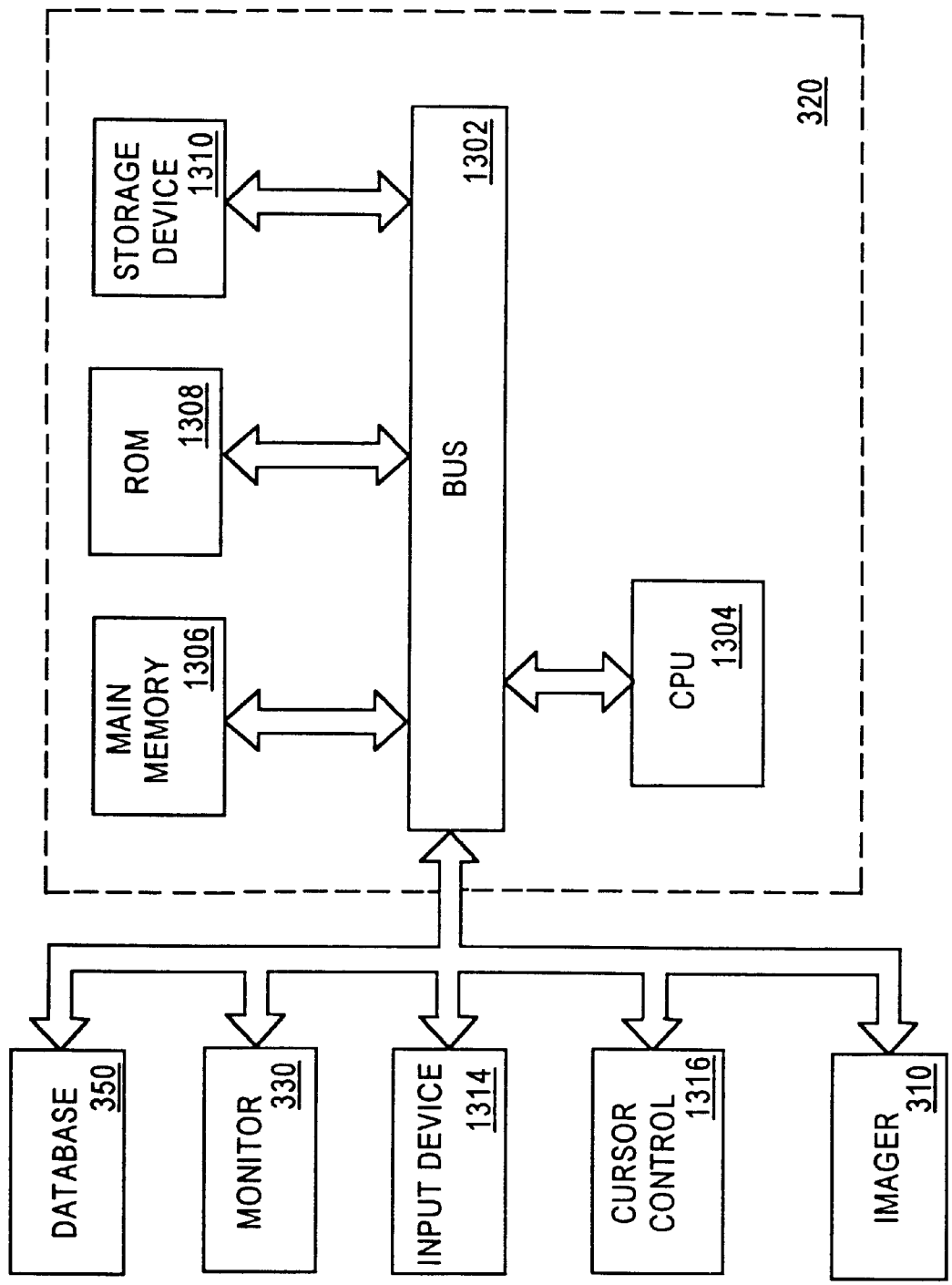
FIG. 13 is a block diagram that illustrates an embodiment of the invention.

FIG. 13 is a block diagram that illustrates an embodiment of the invention shown in FIG. 3. According to this embodiment, processor 320, as shown in FIG. 3, includes a bus 1302 or other communication mechanism for communicating information, and a central processing unit (CPU) 1304 coupled with bus 1302 for processing information. Processor 320 also includes a main memory 1306, such as a random access memory (RAM) or other dynamic storage device, coupled to bus 1302 for storing information and instructions to be executed by CPU 1304. Main memory 1306 also may be used for storing temporary variables or other intermediate information during execution of instructions to be executed by CPU 1304. Processor 320 further includes a read only memory (ROM) 1308 or other static storage device coupled to bus 1302 for storing static information and instructions for CPU 1304. A storage device 1310, such as a magnetic disk or optical disk, is coupled to bus 1302 for storing information and instructions. Storage device 1310 may also serve as memory 340 in FIG. 3.

Processor 320 is coupled, as via bus 1302, to monitor 330 (FIG. 3), such as a cathode ray tube (CRT), for displaying information to the user. An input device 1314, including alphanumeric and other keys, is coupled to bus 1302 for communicating information and command selections to CPU 1304. Another type of user input device is cursor control 1316, such as a mouse, a trackball, or cursor direction keys for communicating direction information and command selections to CPU 1304 and for controlling cursor movement on monitor 330.

Imager 310 (FIG. 3) inputs data representative of images of a reticle under inspection, as discussed above, to bus 1302. Such data may be stored in main memory 1306 and/or storage device 340, and used by CPU 1304 as it executes instructions. Imager 310 may also receive instructions via bus 1302 from CPU 1304.

Likewise, database 350 (FIG. 3) inputs data representative of a substantially defectless reticle, as discussed above, to bus 1302. Such data may be stored in main memory 1306 and/or storage device 340, and used by CPU 1304 as it executes instructions.

The invention is related to the use of processor 320 for inspecting the surface of a reticle. According to an embodiment of the invention, inspection of the reticle is provided by processor 320 in response to CPU 1304 executing one or more sequences of one or more instructions contained in main memory 1306. Such instructions may be read into main memory 1306 from another computer-readable medium, such as storage device 1310. Execution of the sequences of instructions contained in main memory 1306 causes CPU 1304 to perform the process steps described above. One or more processors in a multi-processing arrangement may also be employed to execute the sequences of instructions contained in main memory 1306. As discussed above, in alternative embodiments, hard-wired circuitry may be used in place of or in combination with software instructions to implement the invention. Thus, embodiments of the invention are not limited to any specific combination of hardware circuitry and software. The programming of the apparatus is readily accomplished by one of ordinary skill in the art provided with the flow charts of FIGS. 2, 5, 6, 8 and 11.

The term "computer-readable medium" as used herein refers to any medium that participates in providing instructions to CPU 1304 for execution. Such a medium may take many forms, including but not limited to, non-volatile media, volatile media, and transmission media. Non-volatile media include, for example, optical or magnetic disks, such as storage device 1310. Volatile media include dynamic memory, such as main memory 1306. Transmission media include coaxial cable, copper wire and fiber optics, including the wires that comprise bus 1302. Transmission media can also take the form of acoustic or light waves, such as those generated during radio frequency (RF) and infrared (IR) data communications. Common forms of computer-readable media include, for example, a floppy disk, a flexible disk, hard disk, magnetic tape, any other magnetic medium, a CD-ROM, DVD, any other optical medium, punch cards, paper tape, any other physical medium with features of holes, a RAM, a PROM, and EPROM, a FLASH-EPROM, any other memory chip or cartridge, or any other medium from which a computer can read.

Various forms of computer-readable media may be involved in carrying out one or more sequences of one or more instructions to CPU 1304 for execution. For example, the instructions may initially be borne on a magnetic disk of a remote computer. The remote computer can load the instructions into its dynamic memory and send the instructions over a telephone line using a modem.

A modem local to processor 320 can receive the data on the telephone line and use an infrared transmitter to convert the data to an infrared signal. An infrared detector coupled to bus 1302 can receive the data carried in the infrared signal and place the data on bus 1302. Bus 1302 carries the data to main memory 1306, from which CPU 1304 retrieves and executes the instructions. The instructions received by main memory 1306 may optionally be stored on storage device 1310 either before or after execution by CPU 1304.

Thus, the methodology of the present invention enables accurate and reliable inspection of an isolated feature by identifying all the pixels and only he pixels, whole and partial, that are part of the isolated feature, and then calculating significant feature parameters (e.g., energy and scatter values) to obtain a signature for the feature. This avoids the pixel-by-pixel comparison inspection of conventional reticle inspection tools, which can miss small features or give inaccurate results. Furthermore, by calculating comparable parameter values for a reference feature at substantially the same location on the reticle as the inspected feature, the inspected feature is identified as being a particular type of isolated feature out of a predefined "collection" of features, without the need for perfect registration between the reference channel and the inspected channel, thereby reducing inspection time. The parameters of the inspected feature are then compared to comparable parameters in a historical database of previously inspected features to detect defects, and can be added to the historical database if a defect is not found. Moreover, if the inspected and reference isolated features cannot be identified as being in the collection of features, they can be added to the collection as representative of a new feature.

The present invention is applicable to the inspection of any photolithographic reticle used in the manufacture of semiconductor devices, and is especially useful for in-process inspection of reticles used in the manufacture of high density semiconductor devices with submicron design features.

The present invention can be practiced by employing conventional materials, methodology and equipment. Accordingly, the details of such materials, equipment and methodology are not set forth herein in detail. In the previous descriptions, numerous specific details are set forth, such as specific materials, structures, chemicals, processes, etc., in order to provide a thorough understanding of the present invention. However, it should be recognized that the present invention can be practiced without resorting to the details specifically set forth. In other instances, well known processing structures have not been described in detail, in order not to unnecessarily obscure the present invention.

Only the preferred embodiment of the present invention and but a few examples of its versatility are shown and described in the present disclosure. It is to be understood that the present invention is capable of use in various other combinations and environments and is capable of changes or modifications within the scope of the inventive concept as expressed herein.

What is claimed is:

1. A method of inspecting a target feature formed on a surface, which method comprises:
    imaging the target feature to produce one or more target data elements representative of the target feature, each target data element having a gray level and associated with a respective location on the surface;
    isolating the target feature;
    calculating a value of a parameter of the isolated target feature;
    identifying the target feature as corresponding to a target reference feature; and
    comparing the target feature parameter value with a corresponding parameter value associated with the target reference feature to determine whether a defect exists in the target feature;
    wherein calculating the target feature parameter value comprises calculating an energy value for the target feature by summing the gray levels of the target data elements corresponding to the target feature, and calculating scatter values for the target feature in several directions, each scatter value based on a moment of inertia with respect to an equilibrium center of the target feature.

2. The method of claim 1, comprising imaging the target feature with a charge coupled device (CCD).

3. The method of claim 2, comprising one of imaging the target feature by transmitting light through the target feature to the CCD and reflecting light from the target feature to the CCD.

4. The method of claim 1, wherein the target feature includes feature surfaces and edges, and each target data element represents one of a feature surface associated with the target data element gray level and an edge of the target feature, further comprising:
    determining the target feature edges in the target data elements;
    calculating a percentage of each target data element which contains a portion of the target feature based on the determination of the target feature edges; and
    multiplying the gray level and the percentage of each target data element to obtain the weighted gray levels of the target data elements corresponding to the target feature.

5. The method of claim 4, comprising determining the target feature edges using the canny method.

6. The method of claim 4, wherein the surface comprises a plurality of spaced-apart features which includes the target feature, the method comprising:
    imaging the plurality of features to produce an array of feature data elements representative of the features and background data elements representative of space separating the features;
    selecting one of the target data elements; and
    determining all the target data elements representative of the target feature by analyzing the data elements surrounding the selected target data element to identify a frame of contiguous background data elements surrounding all the target data elements and only the target data elements.

7. The method of claim 6, comprising assigning the background data elements a first binary value and the feature data elements a second binary value prior to the determining step based on their respective gray levels, wherein the determining step comprises identifying the frame by searching for data elements having the first binary value.

8. The method of claim 6, wherein the step of identifying the target feature as corresponding to the target reference feature comprises:
    receiving an array of reference data elements from a reference database, the reference data elements representative of a plurality of spaced-apart features which includes the target reference feature and background data elements representative of space separating the features, each reference data element having a gray level, the target reference feature data elements corresponding to substantially the same location on the surface as the target data elements;
    selecting one of the target reference data elements;
    determining all the data elements representative of the target reference feature by analyzing the data elements surrounding the selected target reference data element to identify a frame of contiguous background data elements surrounding all the target reference data elements and only the target reference data elements;

selecting a target reference data element inside the frame;

selecting a feature data element corresponding to the location of the selected target reference data element; and analyzing the selected feature data element and a plurality of feature data elements surrounding the selected feature data element to determine whether the selected feature data element or one of the plurality of surrounding feature data elements is a target feature data element.

9. The method of claim 8, comprising determining that a missing feature defect exists on the surface when none of the selected feature data element or the plurality of surrounding feature data elements is a target feature data element.

10. The method of claim 8, wherein when the selected feature data element or one of the plurality of surrounding feature data elements is a target feature data element, the method comprising calculating the target reference feature parameter value.

11. The method of claim 10, comprising:

comparing the target reference feature parameter value to a plurality of feature identification parameter values, each feature identification parameter value being associated with a respective historical database of parameter values of previously inspected target features; and determining a defect exists in the target feature when the target reference feature parameter value substantially matches one of the feature identification parameter values, and the target feature parameter value deviates from the historical database parameter value associated with the matching feature identification parameter value more than a predetermined threshold value.

12. The method of claim 11, comprising adding the target feature parameter value to the historical database associated with the matching feature identification parameter value when no defect is found to exist in the target feature, and the target feature parameter value does not deviate from the historical database parameter value associated with the matching feature identification parameter value more than a predetermined updating threshold value.

13. The method of claim 11, wherein when the target reference feature parameter value does not substantially match one of the feature identification parameter value, the method comprises:

forming an additional feature identification parameter value based on the target reference feature parameter value; and forming an additional historical database associated with the additional feature identification parameter value based on the target feature parameter value.

14. The method of claim 10, wherein calculating the target reference feature parameter value comprises:

calculating an energy value for the target reference feature by summing the gray levels of the reference data elements corresponding to the target reference feature; and calculating a scatter value for the target reference feature in a predetermined direction in the target reference feature.

15. The method of claim 1, comprising:

calculating a projection of each of the target data elements in the target feature;

calculating the center of equilibrium of the target feature with respect to the origin based on the projection of each of the target data elements;

calculating a moment of inertia of the target feature about an axis that passes through the origin;

calculating moments of inertia of the target feature about an axis that passes through the center of equilibrium; and calculating the scatter values for the target feature about the axis that passes through the center of equilibrium.

16. The method of claim 1, wherein the target reference feature parameter value is received from a historical database of previously inspected target features, the method comprising determining a defect exists in the target feature when the target feature parameter value deviates from a corresponding historical database parameter value more than a predetermined threshold value.

17. The method of claim 1, wherein the target feature parameter value corresponds to at least one of a height of the target feature, a width of the target feature, the perimeter of the target feature, a diameter of the target feature, a radius of the target feature, the energy of the target feature, and a scatter value of the target feature.

18. A method of inspecting a target feature formed on a surface, which method comprises:

imaging the target feature to produce one or more target data elements representative of the target feature, each target data element having a gray level and associated with a respective location on the surface;

isolating the target feature;

calculating a value of a parameter of the isolated target feature;

identifying the target feature as corresponding to a target reference feature; and comparing the target feature parameter value with a corresponding parameter value associated with the target reference feature to determine whether a defect exists in the target feature;

wherein calculating the target feature parameter value comprises calculating an energy value for the target feature by summing the gray levels of the target data elements corresponding to the target feature, and calculating a plurality of scatter values for the target feature based on an equilibrium center of the target feature, each scatter value calculated in a different predetermined direction in the target feature;

wherein calculating the scatter values comprises:

calculating the projection of each of the target data elements in the predetermined directions in the target feature;

calculating the center of equilibrium of the target feature with respect to the origin based on the projection of each of the target data elements;

calculating moments of inertia of the target feature about axes in the predetermined directions that pass through the origin;

calculating moments of inertia of the target feature about axes in the predetermined directions that pass through the center of equilibrium; and calculating the scatter values for the target feature about the axes in the predetermined directions that pass through the center of equilibrium.

19. The method of claim 18, wherein the predetermined directions in the target feature comprise arbitrary directions.

20. The method of claim 18, wherein the predetermined directions in the target feature comprise at least one of a horizontal direction, vertical direction, slash direction and backslash direction.

21. A computer-readable medium bearing instructions for inspecting a target feature formed on a surface, said instructions, when executed, being arranged to cause one or more processors to perform the steps of:

controlling an imager to image the target feature to produce one or more target data elements representative of the target feature, each target data element having a gray level and associated with a respective location on the surface;

isolating the target feature;

calculating a value of a parameter of the isolated target feature;

identifying the target feature as corresponding to a target reference feature; and comparing the target feature parameter value with a corresponding parameter value associated with the target reference feature to determine whether a defect exists in the target feature;

wherein calculating the value of the parameter of the isolated target feature comprises calculating an energy value for the target feature by summing the gray levels of the target data elements corresponding to the target feature, and calculating scatter values for the target feature in several directions, each scatter value based on a moment of inertia with respect to an equilibrium center of the target feature.

22. The computer-readable medium according to claim 21, wherein the target feature includes feature surfaces and edges, and each target data element represents one of a feature surface associated with the target data element gray level and an edge of the target feature, wherein the instructions, when executed, are arranged to cause the one or more processors to perform the steps of:

determining the target feature edges in the target data elements;

calculating a percentage of each target data element which contains a portion of the target feature based on the determination of the target feature edges; and multiplying the gray level and the percentage of each target data element to obtain the weighted gray levels of the target data elements corresponding to the target feature.

23. The computer-readable medium according to claim 22, wherein the instructions, when executed, are arranged to cause the one or more processors to perform the step of detecting the target feature edges using the canny method.

24. The computer-readable medium according to claim 23, wherein when the target reference feature parameter value does not substantially match one of the feature identification parameter values, the instructions, when executed, are arranged to cause the one or more processors to perform the steps of:

forming an additional feature identification parameter value based on the target reference feature parameter value; and forming an additional historical database associated with the additional feature identification parameter value based on the target feature parameter value.

25. The computer-readable medium according to claim 22, wherein the surface comprises a plurality of spaced-apart features which includes the target feature, wherein the instructions, when executed, are arranged to cause the one or more processors to perform the steps of:

controlling the imager to image the plurality of features to produce an array of feature data elements representative of the features and background data elements representative of space separating the features;

selecting one of the target data elements; and determining all the target data elements representative of the target feature by analyzing the data elements surrounding the selected target data element to identify a frame of contiguous background data elements surrounding all the target data elements and only the target data elements.

26. The computer-readable medium according to claim 25, wherein the instructions, when executed, are arranged to cause the one or more processors to perform the steps of:

assigning the background data elements a first binary value and the feature data elements a second binary value prior to the determining step based on their respective gray levels; and identifying the frame by searching for data elements having the first binary value.

27. The computer-readable medium according to claim 25, wherein the instructions, when executed, are arranged to cause the one or more processors to identify the target feature as corresponding to the target reference feature by performing the steps of:

receiving an array of reference data elements from a reference database, the reference data elements representative of a plurality of spaced-apart features which includes the target reference feature and background data elements representative of space separating the features, each reference data element having a gray level, the target reference feature data elements corresponding to substantially the same location on the surface as the target data elements;

selecting one of the target reference data elements;

determining all the data elements representative of the target reference feature by analyzing the data elements surrounding the selected target reference data element to identify a frame of contiguous background data elements surrounding all the target reference data elements and only the target reference data elements;

selecting a target reference data element inside the frame;

selecting a feature data element corresponding to the location of the selected target reference data element; and analyzing the selected feature data element and a plurality of feature data elements surrounding the selected feature data element to determine whether the selected feature data element or one of the plurality of surrounding feature data elements is a target feature data element.

28. The computer-readable medium according to claim 27, wherein the instructions, when executed, are arranged to cause the one or more processors to perform the step of determining that a missing feature defect exists on the surface when none of the selected feature data elements or the plurality of surrounding feature data elements is a target feature data element.

29. The computer-readable medium of claim 27, wherein when the selected feature data element or one of the plurality of surrounding feature data elements is a target feature data element, the instructions, when executed, are arranged to cause the one or more processors to perform the step of calculating the target reference feature parameter value.

30. The computer-readable medium according to claim 29, wherein the instructions, when executed, are arranged to cause the one or more processors to perform the steps of:

comparing the target reference feature parameter value to a plurality of feature identification parameter values, each feature identification parameter value being associated with a respective historical database of parameter values of previously inspected target features; and determining a defect exists in the target feature when the target reference feature parameter value substantially matches one of the feature identification parameter values, and the target feature parameter value deviates from the historical database parameter value associated with the matching feature identification parameter value more than a predetermined threshold value.

31. The computer-readable medium according to claim 30, wherein the instructions, when executed, are arranged to cause the one or more processors to perform the step of adding the target feature parameter value to the historical database associated with the matching feature identification parameter value when no defect is found to exist in the target feature, and the target feature parameter value does not deviate from the historical database parameter value associated with the matching feature identification parameter value more than a predetermined updating threshold value.

32. The computer-readable medium according to claim 29, wherein the instructions, when executed, are arranged to cause the one or more processors to perform the step of calculating the target reference feature parameter value by:

calculating an energy value for the target reference feature by summing the gray levels of the reference data elements corresponding to the target reference feature; and calculating a scatter value for the target reference feature in a predetermined direction in the target reference feature.

33. The computer-readable medium according to claim 21, wherein the instructions, when executed, are arranged to cause the one or more processors to perform the steps of:

calculating a projection of each of the target data elements in the target feature;

calculating the center of equilibrium of the target feature with respect to the origin based on the projection of each of the target data elements;

calculating a moment of inertia of the target feature about an axis that passes through the origin;

calculating moments of inertia of the target feature about an axis that passes through the center of equilibrium; and calculating the scatter values for the target feature about the axis that passes through the center of equilibrium.

34. The computer-readable medium of claim 21, wherein the target reference feature parameter value is received from a historical database of previously inspected target features, wherein the instructions, when executed, are arranged to cause the one or more processors to perform the step of determining a defect exists in the target feature when the target feature parameter value deviates from a corresponding historical database parameter value more than a predetermined threshold value.

35. The computer-readable medium according to claim 21, wherein the target feature parameter value corresponds to at least one of a height of the target feature, a width of the target feature, the perimeter of the target feature, a diameter of the target feature, a radius of the target feature, the energy of the target feature, and a scatter value of the target feature.

36. A computer-readable medium bearing instructions for inspecting a target feature formed on a surface, said instructions, when executed, being arranged to cause one or more processors to perform the steps of:

controlling an imager to image the target feature to produce one or more target data elements representative of the target feature, each target data element having a gray level and associated with a respective location on the surface;

isolating the target feature;

calculating a value of a parameter of the isolated target feature;

identifying the target feature as corresponding to a target reference feature; and comparing the target feature parameter value with a corresponding parameter value associated with the target reference feature to determine whether a defect exists in the target feature;

wherein calculating the value of the parameter of the isolated target feature comprises summing the gray levels of the target data elements corresponding to the target feature, and calculating a plurality of scatter values for the target feature based on an equilibrium center of the target feature, each scatter value calculated in a different predetermined direction in the target feature; and the instructions, when executed, are arranged to cause the one or more processors to perform the step of calculating the scatter values by:

calculating the projection of each of the target data elements in the predetermined directions in the target feature;

calculating the center of equilibrium of the target feature with respect to the origin based on the projection of each of the target data elements;

calculating moments of inertia of the target feature about axes in the predetermined directions that pass through the origin;

calculating moments of inertia of the target feature about axes in the predetermined directions that pass through the center of equilibrium; and calculating the scatter values for the target feature about the axes in the predetermined directions that pass through the center of equilibrium.

37. The computer-readable medium according to claim 36, wherein the predetermined directions in the target feature comprise arbitrary directions.

38. The computer-readable medium according to claim 36, wherein the predetermined directions in the target feature comprise at least one of a horizontal direction, vertical direction, slash direction and backslash direction.

39. An inspection tool for inspecting a target feature formed on a surface, the inspection tool comprising:

an imager for imaging the target feature to produce one or more target data elements representative of the target feature, each target data element having a gray level and associated with a respective location on the surface; and a processor for isolating the target feature, calculating a value of a parameter of the isolated target feature, and determining if a defect exists in the target feature responsive to the target feature parameter value;

wherein the processor is further configured to:

calculate an energy value for the target feature by summing the gray levels of the target data elements corresponding to the target feature; and calculate scatter values for the target feature in several directions, each scatter value based on a moment of inertia with respect to an equilibrium center of the target feature.

40. The inspection tool of claim 39, wherein the processor is further configured to identify the target feature as corresponding to a target reference feature, the inspection tool further comprising a comparator for comparing the target feature parameter value with a corresponding parameter value associated with the target reference feature to determine whether a defect exists in the target feature.

41. The inspection tool of claim 40, wherein the target feature includes feature surfaces and edges, and each target data element represents one of a feature surface associated with the target data element gray level and an edge of the target feature, wherein the processor is further configured to:
   determine the target feature edges in the target data elements;
   calculate a percentage of each target data element which contains a portion of the target feature based on the determination of the target feature edges; and
   multiply the gray level and the percentage of each target data element to obtain the weighted gray levels of the target data elements corresponding to the target feature.

42. The inspection tool of claim 41, wherein the processor is further configured to determine the target feature edges using the canny method.

43. The inspection tool of claim 41, wherein the surface comprises a plurality of spaced-apart features which includes the target feature;
   wherein the imager is for imaging the plurality of features to produce an array of feature data elements representative of the features and background data elements representative of space separating the features; and
   wherein the processor is further configured to select one of the target data elements and to determine all the target data elements representative of the target feature by analyzing the data elements surrounding the selected target data element to identify a frame of contiguous background data elements surrounding all the target data elements and only the target data elements.

44. The inspection tool of claim 43, wherein the processor is further configured to assign the background data elements a first binary value and the feature data elements a second binary value prior to the determining step based on their respective gray levels, and to identify the frame by searching for data elements having the first binary value.

45. The inspection tool of claim 43, wherein the processor is further configured to identify the target feature as corresponding to the target reference feature by:
   receiving an array of reference data elements from a reference database, the reference data elements representative of a plurality of spaced-apart features which includes the target reference feature and background data elements representative of space separating the features, each reference data element having a gray level, the target reference feature data elements corresponding to substantially the same location on the surface as the target data elements;
   selecting one of the target reference data elements;
   determining all the data elements representative of the target reference feature by analyzing the data elements surrounding the selected target reference data element to identify a frame of contiguous background data elements surrounding all the target reference data elements and only the target reference data elements;
   selecting a target reference data element inside the frame;
   selecting a feature data element corresponding to the location of the selected target reference data element; and
   analyzing the selected feature data element and a plurality of feature data elements surrounding the selected feature data element to determine whether the selected feature data element or one of the plurality of surrounding feature data elements is a target feature data element.

46. The inspection tool of claim 45, wherein the processor is further configured to determine that a missing feature defect exists on the surface when none of the selected feature data element or the plurality of surrounding feature data elements is a target feature data element.

47. The inspection tool of claim 45, wherein when the selected feature data element or one of the plurality of surrounding feature data elements is a target feature data element, the processor is further configured to calculate the target reference feature parameter value.

48. The inspection tool of claim 47, wherein the comparator is further configure to compare the target reference feature parameter value to a plurality of feature identification parameter values, each feature identification parameter value being associated with a respective historical database of parameter values of previously inspected target features; and
   wherein the processor is further configured to determine a defect exists in the target feature when the target reference feature parameter value substantially matches one of the feature identification parameter values, and the target feature parameter value deviates from the historical database parameter value associated with the matching feature identification parameter value more than a predetermined threshold value.

49. The inspection tool of claim 48, wherein the processor is further configured to add the target feature parameter value to the historical database associated with the matching feature identification parameter value when no defect is found to exist in the target feature, and the target feature parameter value does not deviate from the historical database parameter value associated with the matching feature identification parameter value more than a predetermined updating threshold value.

50. The inspection tool of claim 48, wherein when the target reference feature parameter value does not substantially match the feature identification parameter value, the processor is further configured to:
   form an additional feature identification parameter value based on the target reference feature parameter value; and
   form an additional historical database associated with the additional feature identification parameter value based on the target feature parameter value.

51. The inspection tool of claim 47, wherein the processor is further configured to calculate the target reference feature parameter value by:
   calculating an energy value for the target reference feature by summing the gray levels of the reference data elements corresponding to the target reference feature; and
   calculating a scatter value for the target reference feature in a predetermined direction in the target reference feature.

52. The inspection tool of claim 40, wherein the target reference feature parameter value is received from a historical database of previously inspected target features;
   wherein the processor is further configured to determine a defect exists in the target feature when the target feature parameter value deviates from a corresponding historical database parameter value more than a predetermined threshold value.

53. The inspection tool of claim 39, wherein the imager comprises a CCD.

54. The inspection tool of claim 53, wherein the imager images the target feature by transmitting light through the target feature to the CCD, reflecting light from the target feature to the CCD, or both.

55. The inspection tool of claim 39, wherein the processor is further configured to:
- calculate a projection of each of the target data elements in the target feature;
- calculate the center of equilibrium of the target feature with respect to the origin based on the projection of each of the target data elements;
- calculate a moment of inertia of the target feature about an axis that passes through the origin;
- calculate moments of inertia of the target feature about an axis that passes through the center of equilibrium; and
- calculate the scatter values for the target feature about the axis that passes through the center of equilibrium.

56. The inspection tool of claim 39, wherein the target feature parameter value corresponds to at least one of a height of the target feature, a width of the target feature, the perimeter of the target feature, a diameter of the target feature, a radius of the target feature, the energy of the target feature, and a scatter value of the target feature.

57. An inspection tool for inspecting a target feature formed on a surface, the inspection tool comprising:
- an imager for imaging the target feature to produce one or more target data elements representative of the target feature, each target data element having a gray level and associated with a respective location on the surface; and
- a processor for isolating the target feature, calculating a value of a parameter of the isolated target feature, and determining if a defect exists in the target feature responsive to the target feature parameter value;
- wherein the processor is further configured to calculate the target feature parameter value by calculating an energy value for the target feature by summing the gray levels of the target data elements corresponding to the target feature, and calculating a plurality of scatter values for the target feature based on an equilibrium center of the target feature, each scatter value calculated in a different predetermined direction in the target feature;
- wherein the processor is further configured to calculate the scatter values by:
  - calculating the projection of each of the target data elements in the predetermined directions in the target feature;
  - calculating the center of equilibrium of the target feature with respect to the origin based on the projection of each of the target data elements;
  - calculating moments of inertia of the target feature about axes in the predetermined directions that pass through the origin;
  - calculating moments of inertia of the target feature about axes in the predetermined directions that pass through the center of equilibrium; and
  - calculating the scatter values for the target feature about the axes in the predetermined directions that pass through the center of equilibrium.

58. The inspection tool of claim 57, wherein the predetermined directions in the target feature comprise arbitrary directions.

59. The inspection tool of claim 57, wherein the predetermined directions in the target feature comprise at least one of a horizontal direction, vertical direction, slash direction and backslash direction.

* * * * *